United States Patent [19]

Magerlein

[11] Patent Number: 4,837,318
[45] Date of Patent: Jun. 6, 1989

[54] CARBONATE SUBSTITUTED MONOBACTAMS AS ANTIBIOTICS

[75] Inventor: Barney J. Magerlein, Portage, Mich.

[73] Assignee: The Upjohn Company, Kalamazoo, Mich.

[21] Appl. No.: 29,507

[22] Filed: Feb. 6, 1987

Related U.S. Application Data

[63] Continuation-in-part of Ser. No. 732,465, May 9, 1985, abandoned.

[51] Int. Cl.[4] ............... C07D 205/08; C07D 417/12; A61K 31/395; A61K 31/425
[52] U.S. Cl. .................................. 540/355; 540/364
[58] Field of Search ......................................... 540/355

[56] References Cited

U.S. PATENT DOCUMENTS 4,478,749 10/1984 Koster ................................ 540/364

FOREIGN PATENT DOCUMENTS 76758 4/1983 European Pat. Off. .
96297 12/1983 European Pat. Off. .
2515182 4/1983 France .

*Primary Examiner*—Mark L. Berch

[57] ABSTRACT

This invention concerns 2-oxoazetidine analogs (monobactams) having antimicrobial activity, novel processes and novel intermediates useful to make monobactams.

The compounds of this invention include compounds of the formula:

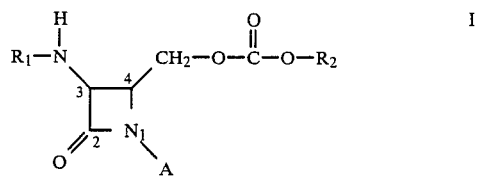

or a pharmaceutically acceptable salt thereof, wherein: $R_1$ is an acyl group derived from a carboxylic acid; A is either sulfo, phosphono or a trisubstituted silyl group substituted with ($C_1$–$C_4$) alkyls or phenyl; $R_2$ is selected from the group consisting of a. ($C_1$–$C_8$) alkyl; b. ($C_2$–$C_8$) alkenyl; c. ($C_3$–$C_8$) alkynyl; d. ($C_3$–$C_8$) cycloalkyl; e. ($C_6$–$C_8$) aryl; f. ($C_6$–$C_{12}$) aralkyl; g. heterocyclic radicals, where each member of (a) through (g) may be substituted by 1 to 4 substituents selected from group consisting of methoxy, hydroxy, halogen, nitro, and —N($R_{10}$)($R_{11}$) wherein $R_{10}$ is hydrogen or alkyl ($C_1$–$C_4$) and $R_{11}$ is hydrogen, alkyl ($C_1$–$C_4$) or alkoxy ($C_1$–$C_4$) provided that when $R_{11}$ is alkoxy, $R_{10}$ must be hydrogen; and h. $(CH_2)_nCH_2X$ where n is 1 to 4 and X is —$OR_3$ where $R_3$ is selected from the group consisting of hydrogen, ($C_1$–$C_4$) alkyl, ($C_2$–$C_3$) alkoxyalkyl and ($C_2$–$C_4$) alkylcarbonyl or X is ($C_2$–$C_4$) alkylcarbonylamino.

8 Claims, No Drawings

4,837,318

CARBONATE SUBSTITUTED MONOBACTAMS AS ANTIBIOTICS

This application is a continuation-in-part of International Application No. PCT/US86/00919, filed Apr. 25, 1986, which a continuation-in-part of U.S. application Ser. No. 732,465, filed May 9, 1985, now abandoned.

FIELD OF THE INVENTION

This invention concerns novel 2-oxazetidine analogs (monobactams) having antimicrobial activity, novel processes to make monobactams and novel intermediates.

INFORMATION DISCLOSURE

Analogs of 2-oxoazetidine derivatives having antimicrobial activity are known in the art. Takeda, European Patent Application Nos. 53-815 and 53-816. Squibb, U.S. Pat. No. 4,478,479 and European Patent Application No. 76-7582A. Among the known monobactam analogs are those containing an O-substituted 2-aminothiazolyl-2-hydroxyiminoactamido group on the C-3 position of the monobactam ring. Roussel UCLAF, European Patent Application No. 114-128-A. Various substituents have been described for the C-4 position of the monobactam ring. Takeda Patent Application EP No. 53-816. However, no publication, patent or patent application known to applicant describes or suggests the substituted monobactams disclosed herein.

SUMMARY OF THE INVENTION

The present invention concerns novel carbonate substituted 2-oxo-azetidine analogs and their use as microbial growth inhibitors. Novel intermediates and processes are also disclosed.

As illustrated in the formula chart, the present invention provides for both "racemic" mixtures and optically active isomers of compounds of Formula I wherein:

$R_1$ is an acyl group derived from a carboxylic acid;
A is either sulfo, phosphono or a trisubstituted silyl group substituted with ($C_1$-$C_4$) alkyls or phenyl; and
$R_2$ is selected from the group consisting of:
  a. ($C_1$-$C_8$) alkyl,
  b. ($C_2$-$C_8$) alkenyl,
  c. ($C_3$-$C_8$) alkynyl,
  d. ($C_3$-$C_8$) cycloalkyl,
  e. ($C_6$-$C_8$) aryl,
  f. ($C_6$-$C_{12}$) aralkyl, and
  g. heterocyclic radicals;
where each member (a) through (g) may be substituted by 1 to 4 substituents selected from the group consisting of methoxy, hydroxy, halogen, nitro, and —N($R_{10}$)($R_{11}$) wherein $R_{10}$ is hydrogen or alkyl ($C_1$-$C_4$) and $R_{11}$ is hydrogen, alkyl ($C_1$-$C_4$) or alkoxy ($C_1$-$C_4$) provided that when $R_{11}$ is alkoxy, $R_{10}$ must be hydrogen; and,
  h. (CH$_2$)$_n$CH$_2$X where n is 0 to 4 and X is —OR$_3$ where $R_3$ is selected from the group consisting of hydrogen, ($C_1$-$C_4$) alkyl, ($C_2$-$C_3$) alkoxyalkyl, and ($C_2$-$C_4$) alkylcarbonyl or X is ($C_2$-$C_4$) alkylcarbonylamino.

A detailed description of the acyl groups included in $R_1$ is found in U.S. Pat. No. 4,478,749, column 8, line 41 to column 12, line 50, as those terms are defined at column 7, line 34 through column 8, line 22, all of which is incorporated by reference herein.

Preferred acyl groups of $R_1$ include those which have been used to acylate 6-aminopenicillanic acid, 7-aminocephalosporic acid and their derivatives which can be found in "Chemistry and Biology of $\beta$-Lactam Antibiotics, Vol. 1, R. B. Morin and M. Gorham, ed., Academic Press, N.Y. 1982 and include the following list:

2-Cyanoacetyl,
Aminophenylacetyl,
Amino(4-hydroxyphenyl)acetyl,
α(Thien-2-yl)acetyl,
α(Thien-3-yl)acetyl,
Phenylacetyl,
Hydroxyphenylacetyl,
(Formyloxy)phenylacetyl,
[(Trifluoromethyl)thio]acetyl,
2-(3,5-Dichloro-4-oxo1(4H)-pyridyl)acetyl,
(1H-Tetrazol-1-yl)acetyl,
(2Amino-4-thiazolyl)-2-methoxyimninoacetyl,
2-[(Cyanomethyl)thio]acetyl,
[[(4-Ethyl-2,3-dioxo-1-piperazinyl)carbonyl]amino]-phenylacetyl,
[[(4-Ethyl-2,3-dioxo-piperazinyl)carbonyl]amino](4-hydroxyphenyl)acetyl,
2-(Aminomethyl)phenylacetyl,
4-(Carbamoylcarboxymethylene)-1,3-dithiethane-2-carbonyl,
3-(o-Chlorophenyl)-5-methyl-4-isoxazolecarbonyl,
2-p-[(1,4,5,6-Tetrahydro-2-pyrimidinyl(phenyl]acetyl,
Amino-1,4-cyclohexadien-1-yl-acetyl,
Phenylsulfoacetyl,
(2R)-2-amino-2-(m-methanesulfonamidophenyl)acetyl,
(2-Amino-4-thiazolyl)-2-(1-carboxy-1-methylethoxy)iminoacetyl,
2-(1H-Tetrazol-1-yl)acetyl,
(2,3-Dihydro-2-imino-4-thiazolyl)(methoxyimino)acetyl,
(2-Amino-4-thiazol)carboxymethoxyimioacetyl,
(2-Aminopyridin-6-yl)methoxyiminoacetyl,
(2-Aminopyridin-6-yl)carboxymethoxyiminoacetyl,
(4-Amino-2-pyrimidyl)methoxyiminoacetyl,
(5-Amino-1,2,4-thiazol-3-yl)-2-methoxyiminoacetyl,
(5-Amino-1,2,4-thiazol-3-yl)-2-carboxymethoxyimonoacetyl,
(5-Amino-1,2,4-thiazol-3-yl)-1-carboxy-1-methylethoxy)iminoacetyl,
D-α[[(Imidazolidin-2-on-1-yl)-carbonyl]amino]-phenylacetyl,
D-α[[(3-mesyl-imidazolidin-2-on-1-yl)carbonyl]amino]phenylacetyl,
2,6-Dimethylbenzoyl,
(S)-2-(4-hydroxy-1,5-naphthyridine-3-caboxamido-2-phenylacetyl.

The most preferred $R_1$ substituents are the substituted aminothiazolyl oxime-carbonyl substituents shown in formula II wherein:

$R_4$ is selected from the group consisting of: ($C_1$-$C_4$) alkyl, ($C_2$-$C_3$) alkenyl, ($C_3$-$C_4$) alkynyl or substituted ($C_1$-$C_4$) alkyl such that susbstituted refers to 1 to 3 members of the following groups, amino, bromo, carboxy, chloro, cyano, fluoro, hydroxy, ($C_2$-$C_4$) alkoxycarbonyl, aminocarbonyl, ($C_1$-$C_3$) alkoxy and ($C_2$-$C_3$) alkylthio;

the substituted oxime is in the syn configuration (Z); and,

R₅ is selected from the group consisting of: hydrogen, t-butoxycarbonyl, phenylmethoxycarbonyl, and triphenylmethyl.

The preferred compounds are the C-3 and C-4 cis isomers of:

3-[2-(2-amino-4-thiazolyl)-(Z)-2-carboxymethoxyiminoacetamido]-4-[(methoxycarbonyl)oxymethyl]-2-oxo-1-azetidinesulfonic acid and the potassium salt thereof;

3-[2-amino-4-thiazolyl)-(Z)-2-methoxyiminoacetamido]-4-[(methoxycarbonyl)oxymethyl]-2-oxo-1-azetidinesulfonic acid and the potassium salt thereof;

3-[2-(2-amino-4-thiazolyl)-(Z)-2-(1-methyl-1-carboxyethoxyimino)acetamido]-4-[(methoxycarbonyl)oxymethyl]-2-oxo-1-azetidinesulfonic acid and the potassium salt thereof;

3-[D(−)-(α)-(4-ethyl-2,3-dioxo-1-piperazinocarbonylamino)phenylacetamido]-4-[(methoxycarbonyl)oxymethyl]-2-oxo-1-azetidinesulfonic acid and the potassium salt thereof;

3-[2-(2-amino-4-thiazolyl)-(Z)-2-carboxymethoxyiminoacetamido]-4-[(phenoxycarbonyl)oxymethyl]-2-oxo-1-azetidinesulfonic acid and the potassium salt thereof;

3-[2-(2-amino-4-thiazolyl)-(Z)-2-carboxymethoxyiminoacetamido]-4-[(methoxyethoxycarbonyl)oxymethyl]-2-oxo-1-azetidinesulfonic acid and the potassium salt thereof;

3-[2-(2-amino-4-thiazolyl)-(Z)-2-carboxymethoxyiminoacetamido]-4-[(formylaminoethoxycarbonyl)oxymethyl]-2-oxo-1-azetidinesulfonic acid and the potassium salt thereof;

3-[2-(2-amino-4-thiazolyl)-(Z)-2-(carboxymethoxyiminoacetamido)]-4-[(chloroethoxycarbonyl)oxymethyl]-2-oxo-1-azetidinesulfonic acid;

3-[2-(2-amino-4-thiazolyl)-(Z)-2-(carboxymethoxyimino-acetamido)]-4-[(aminoethoxycarbonyloxymethyl]-2-oxo-2-azetidinesulfonic acid;

3-[2-(2-amino-4-thiazolyl)-(Z)-2-(carboxymethoxyiminoacetamido)]-4-[(carbamoyloxyethoxycarbonyl)oxomethyl]-2-oxo1-azetidinesulfonic acid; and 3-[2-(2-amino-4-thiazolyl)-(Z)-2-(carboxymethoxyimino-acetamido)]-4-[(i-propoxycarbonyl)oxymethyl]-2-oxo-1-azetidinesulfonic acid.

More particularly preferred are isomers of the above eleven compounds wherein the absolute configuration with respect to carbon centers 3 and 4 is 3(S) and 4(S).

Most preferred are the following four compounds:

(3S,4S)-3-[2-(2-amino-4-thiazolyl)-(Z)-2-carboxymethoxyiminoacetamido]-4-[(methoxycarbonyl)oxymethyl]-2-oxo-1-azetidinesulfonic acid and the potassium salt thereof;

(3S,4S)-3-[2-(2-amino-4-thiazolyl)-(Z)-2-methoxyiminoacetamido]-4-[(methoxycarbonyl)oxymethyl]-2-oxo-1-azetidinesulfonic acid and the potassium salt thereof;

(3S,4S)-3-[2-(2-amino-4-thiazolyl)-(Z)-2-(carboxymethoxyiminoacetamido]-4-[(aminoethoxycarbonyloxymethyl]-2-oxo-2-azetidinesulfonic acid; and (3S,4S)-3-[2-(2-amino-4-thiazolyl)-(Z)-2-[carboxymethoxyiminoacetamido]-4-[(carbamoyloxyethoxycarbonyl)oxomethyl]-2-oxo1-azetidinesulfonic acid.

Finally, a process is disclosed by which carbonate compounds of formula I as defined above are made by converting the C-4 hydroxymethyl compound of formula III.

The various carbon moieties are defined as follows:

Alkyl refers to an aliphatic hydrocarbon radical either branched or unbranched such as methyl, ethyl, n-propyl, isopropyl, n-butyl, isobutyl, sec-butyl, tert-butyl or the like.

Alkoxy refers to an alkyl radical which is attained to the remainder of the molecule by oxygen such as methoxy, ethoxy, n-propoxy, isopropoxy, n-butoxy, isobutoxy, sec-butoxy, tert-butoxy or the like.

Alkenyl refers to a radical of an aliphatic unsaturated hydrocarbons having a double bond and includes both branched and unbranched forms such as vinyl, allyl, isoproponyl, 2-methallyl, 2-butenyl, 3-butenyl or the like.

Alkynyl refers to a radical of an aliphatic unsaturated hydrocarbons having a triple bond and includes both branched and unbranched forms such as 1-propynyl, 2-propynyl, or the like.

Aralkyl refers to a radical in which an aryl group is substituted for a hydrogen atom of an alkyl such as benzyl, phenylethyl, phenylpropyl, diphenylmethyl, fluorenylmethyl and the like.

Aryl refers to a radical derived from an aromatic hydrocarbon by removal of one hydrogen atoms such as phenyl, α-naphthyl, 13-naphthyl, biphenyl, anthryl and the like.

Cycloalkyl refers to a radical of a saturated hydrocarbon in a ring structure such cyclopropyl, cyclobutyl, cyclopentyl, cyclohexyl, cycloheptyl, adamantyl and the like.

Heterocyclic radical refers to 5 to 8-membered heterocyclic rings having one to a few hetero-atoms such as nitrogen (inclusive of N-oxide), oxygen and sulfur, as well as fused rings corresponding thereto, which have an available bonding site at a carbon atom thereof. Examples of such heterocyclic group which are usually advantageous include 2- or 3-pyrrolyl, 2- or 3-furyl, 2- or 3-thienyl, 2- or 3-pyrrolidinyl, 2-, 3- or 4-pyridyl, N-oxido-2-, 3- or 4pyridyl, 2-, 3- or 4-piperidinyl, 2-, 3- or 4-pyranyl, 2-, 3- or 4-thiopyranyl, pyrazinyl, 2-, 4- or 5-thiazolyl, 2-, 4- or 5-oxazolyl, 3-, 4- or 5-isothiazolyl, 3-, 4- or 5-isoxazolyl, 2-, 4- or 5-imidazolyl, 3-, 4- or 5-pyrazolyl, 3- or 4-pyridazinyl, 2-, 4- or 5-pyrimidinyl, piperazinyl, 4- or 5-(1,2,3-thiadiazolyl), 3- or 5-(1,2,4-thiadiazolyl), 1,3,4-thiadiazolyl, 1,2,5-thiadiazolyl, 4- or 5-(1,2,3-oxadiazolyl), 3- or 5-(1,2,4-oxadiazolyl), 1,3,4-oxadiazolyl, 1,2,5-oxadiazolyl, 1,2,3- or 1,2,4-triazolyl, 1H- or 2H-tetrazolyl, pyrido[2,3-d]pyrimidyl, benzopyranyl, 1,8-, 1,5-, 1,6-, 1,7- 2,7- or 2,6-naphthyridyl, quinolyl, thieno[2,3-b]pyridyl and the like.

Syn configuration (Z) refers to the position occupied by two radicals in that type of stereo-isomerism in which they are closer together than in the corresponding antiposition.

Unless otherwise indicated, in the above description and throughout this document: (a) the parenthetical term $(C_n-C_m)$ is inclusive such that a compound of $(C_1-C_4)$ would include compounds of one, two, three and four carbons and their isomeric forms; (b) in substituents specifying carbonyl such as $(C_2-C_4)$ alkylcarbonyl, the prefix $(C_2-C_4)$ includes the carbonyl carbon atom as one of the 4 carbons limiting the total number of carbons in the alkyl to no more than 3; and, (c) where two multiple carbon moieties are present on a substituent such as $(C_2-C_4)$ alkoxyalkyl, the number of carbon atoms in both the alkyl and alkoxy moieties taken together do not exceed 4.

The scope of this invention includes the pharmaceutically acceptable salts of the disclosed compounds. Such salts include the following cations but are not limited to these: alkali metal ions such as potassium, sodium, lithium, alkaline earth metal ions such as magnesium or calcium and ammonium ions such as ammonium, tetralkylammonium and pyridinium.

It will be apparent to those skilled in the art that compounds of the invention herein described may contain several chiral carbons. All of the optically active, enantiomorphic and sterioisomeric forms are included within the scope of this invention. The invention also includes both the individual isomers and mixtures. Specifically the azetidines of this invention (Formula I) have chiral carbon atoms at positions C-3 and C-4 and the $\beta$-lactam ring. The preferred form is cis at centers 3 and 4 and the most preferred is 3(S) and 4(S) with regard to orientation at C-3 and C-4. The phrase "C-3 and C-4 cis isomers" means that the substituents at C-3 and C-4 are both oriented on the same side of the $\beta$-lactam ring.

Compounds of this invention are tested for in vitro antimicrobial activity using standard testing procedures such as the determination of minimum inhibitory concentration (MIC) by agar dilution as described in "Methods for Dilution Antimicrobial Susceptibility Tests for Bacteria that Grow Aerobically" (MFT) published January 1983 by the National Committee for Clinical Laboratory Standards, 771 East Lancaster Avenue, Villanova, PA, USA, 19804. Briefly, MIC values are determined in unsupplemented Mueller Hinton Agar (MHA). The compounds tested are diluted serially into molten MHA at 47° C. The agar is poured into petri dishes and allowed to harden. The various bacterium used for testing are grown overnight on MHA at 35° C. and transferred to Trypticase soy broth (TSB) until a turbidity of 0.5 McFarland standard is obtained. The bacterium are diluted one to twenty in TSB and inoculated on the plates (1 $\mu$l using a Steers replicator). The plates are incubated at 35° C. for 20 hours and the MIC is read to be the lowest concentration of drug that completely inhibits visible growth of the bacterium. The MIC test results of two compounds of this invention are found in Table 1.

DETAILED DESCRIPTION

The process of making compounds of Formula I is illustrated by Charts 1 and 2.

CHART 1

The starting compound, cis-($\pm$)-4-(methoxycarbonyl)-2-oxo-3-[[(phenylmethoxy)carbonyl]amino]-1-azetidine (1) is known. J. Org. Chem. 47: 2765–2767, 1982. It may be cis or trans with respect to the substituents on positions 3 and 4. It is recognized that alternative alkoxycarbonyls ($C_1$–$C_5$) (substituted or unsubstituted) or aralkoxycarbonyls ($C_5$–$C_{14}$) (substituted or unsubstituted) could be used in place of the benzyloxycarbonyl group on compound (I). Substituents would include ($C_1$–$C_4$) alkyl, halogen or nitro where the number of substituents could be one through four.

In Step 1, the nitrogen at position 1 is protected. Silylation is preferred. Silylating agents ($B_2$) well known in the art may be used. Typically, a trialkylsilyl chloride or an araylalkylsilyl chloride in the presence of an organic base is used. The reaction is conducted at a temperature of about 0° to 25° C. for a period of about 1 to 5 hours in any of several anhydrous solvents, e.g., ethyl acetate, dioxane, tetrahydrofuran, methylenedichloride, or dimethylformamide, in the presence of either an inorganic base, or a tertiary amine such as trialkylamine or imidazole. A preferred solvent is dimethylformamide. Compounds (2) can be removed from the reaction mixture by conventional means such as crystallization, filtration, chromatography and combinations thereof.

In Step 2, the protected amino azetidinone (2) is reduced to give the compounds (3). The reaction is conducted in the presence of a metal hydride at a temperature range of 0° to room temperature for times of 2 to 5 hours. The preferred method is to treat compounds (2) with lithium borohydride in anhydrous tetrahydrofuran under cold conditions for several hours. Compounds (3) can be obtained from the reaction mixture by conventional methods such as crystallization, or column chromatography, and combinations thereof.

Compounds (3) can be directly used in Steps 1 or 3 of Chart 2. Alternaively, the benzyloxycarbonyl substituent of compounds (3) can be hydrogenolysed and replaced with alternative blocking groups $B_1$ to yield compounds (4). These alternative steps become preferred when removal of the benzyloxycarbonyl is not practical by hydrogenolysis because other substituents will be simultaneously and undesirably reduced or when a substituent may poison the hydrogenolysis catalyst.

In Step 3 of Chart 1 hydrogenolysis of the C-3 acyl amino substituent (eg. benzyloxycarbonyl) of compounds (3) is carried out in the presence of palladium-black or palladium on a support such as carbon under hydrogen gas to give a 3-amino compound. These amino compounds are then acylated with blocking groups, $B_1$, to obtain compounds (4). The acylation with $B_1$ can be achieved by the use of the various organic reagents known in the art, such as di-t-butyldicarbonate, t-butoxycarbonyl, or 9-fluorenylmethoxycarbonyl. The acylation is preferably achieved by use of dicyclohexylcarbodiimide and 1-hydroxybenzotriazole at cold temperature. Alternatively, compounds (2) may be acylated before reduction such that steps 2 and 3 of Chart 1 are reversed.

CHART 2

In Step 1, the alcohol compounds (3) or (4) from Chart 1 are treated with a chloroformate ester of the formula ClCOOR$_2$ where R$_2$ is defined as above to give the carbonate compounds (6). This is the preferred route to compounds (6). The reaction conditions involve the use of an inert solvent such as methylene dichloride, tetrahydrofuran, or dimethylformamide at $-20°$ C. to 30° C. in the presence of a slight excess of organic base, such as pyridine, 2,4-lutidine, or triethyl amine. Following extractive workups involving successive washes with acid and base, the products are isolated by chromatography or crystallization. Some chloroformate esters are commercially available and others may be prepared according to the teaching of Huntress, "Organic Chlorine Compounds," John Wiley and Sons, Inc., New York, NY, 1948; F. Stain et al., J. Am. Chem. Soc., 72, 1254 (1950), H. G. Ashburm et al., J. Am. Chem. Soc., 60, 2933 (1938). Briefly, the process described in these references is to contact an alcohol with an excess of phosgene either neat or in an organic solvent. After workup, the product is usually isolated by vacuum distillation.

In Steps 2 and 3 an alternative process to compounds (6) is presented. This process is helpful when the desired chloroformate is unavailable. In Step 2, compounds (3) or (4) are placed in a solvent such as methylene dichloride, ethyl acetate, tetrahydrofuran, or acetonitrile containing a slight excess of an organic base, such as pyridine, triethylamine, or 2,4-lutidine. The solution is treated at −20° C. to 30° C. with a solution of phosgene in an inert solvent, such as toluene, benzene or methylene chloride. The intermediate chloroformate (5) is thus formed in situ, but due to possible instability, is not isolated, but treated with a molar equivalent of the given alcohol (R$_2$OH) to yield-carbonate (6). Once again an excess of base is desirable and the reaction is best conducted in an inert solvent at −20° C. to 30° C. This alternative or reversed process is known in the field of steroid chemistry, G. Schubert et al., Die Pharmazie, 35, 453 (1980).

In Step 4, carbonate compounds (6) are unblocked to an intermediate amine. The preferred process is dependent upon the blocking group (B$_1$) that is present. When carbonate (6) is substituted at B$_1$ with phenylmethoxycarbonyl (Cbz), the substrate is dissolved in a suitable solvent such as tetrahydrofuran, ethyl acetate, dimethyl formamide, methanol, or ethanol. Hydrogenolysis in the presence of a hydrogenation catalyst, such as palladium black or palladium on a support, such as carbon, is accomplished by shaking or stirring in an atmosphere of hydrogen, preferably of less than 3 atm. When the reaction is completed, the catalyst is removed by filtration and the filtrate contains a solution of amine (7). If B$_1$ is t-butoxycarbonyl, this blocking group must be removed by acid, such as trifluoroacetic acid, and the amine isolated by evaporation of the reaction mixture. If B$_1$ is 9-fluorenylmethoxycarbonyl, the amine may be obtained by treatment with an organic base, such as piperidine or morpholine. Isolation of amine (7) then may require chromatography. Amines (7) need not be isolated. The total reaction product can be used for conversion to carbonate (8) in Step 5.

In Step 5, amines (7) are converted to the amides (8) where R$_1$ is as defined above. This conversion may be carried out by any of a number of amide or peptide forming reaction sequences such as described in Methoden der Organischem Chemie, Vierte Auflage, Band XV/2, E. Wunch ed., Georg Thieme Verlag, Stuttgart, p 1. A preferred acylation process is the use of approximately molar quantities of a desired acid, 1-hydroxybenzotriazole, and a carbodiimide, such as dicyclohexylcarbodiimide. These reagents are added to the solution of the amine in a solvent, such as tetrahydrofuran, dimethylformamide, or acetonitrile. A temperature of 0° C.-60° C. is operative, with 20°-35° C. preferred. The time of reaction is variable from 0.5-24 hr being required, although usually 3-4 hr is sufficient. A precipitate of dicyclohexylurea is formed during the reaction. This is removed by filtration. The amides (8) are isolated from the filtrate by extractive procedures and chromatography.

As would be recognized by one skilled in the art, R$_1$ may require blocking groups such as t-butoxycarbonyl, t-butyl, or triphenylmethyl to avoid formation of undesirable sulfonates during Step 6.

In Step 6, the amides (8) are sulfonated at N-1. The amides (8) are dissolved or suspended in a suitable solvent such as dimethylformamide or methylene dichloride and 1-3 equivalents of a sulfonating agent added. The preferred reagent is dimethylformamide-sulfur trioxide complex usually used as an approximately 1 molar solution in dimethyl formamide, K. Hofman and G. Simchen, Synthesis, 699-700 (1979). Pyridine-SO$_3$ complex is also operative. When the reaction is complete, the reaction mixture is diluted with water or phosphate buffer, n-tetrabutylammonium bisulfate added, and the sulfonated azetidine (9) is extracted with a water immiscible solvent, such as methylene dichloride.

Finally, any blocking groups on R$_1$ are generally removed by treatment with acid. In the preferred method an excess of trifluoroacetic acid is added to a solution of the substrate while stirring in an ice bath. The residue resulting from evaporation of the solvent affords the n-tetrabutylammonium salt which is dissolved in water (a small volume of methanol may be added to hasten solution) and passed through a column of Dowex-50 resin in the K$^+$ form. The column is washed with water. This eluant, now as the potassium salt, is passed over a column of HP-20 resin (Mitsubishi Chemical Industries). This column is eluted and combined as described in the experimental section resulting in the obtention of monobactam (9).

Optically active isomers of the disclosed compounds are resolved by methods known in the art. Takeda European patent application No. 8310461-3. Typically the separation of enantiomers is carried out by forming salts with enantiomers of a tartaric acid and taking advantage of the difference in solubility between the resulting diastereomers. The starting compound, cis-(±)-1[(2,4-dimethoxyphenyl)methyl]-4-(methoxycarbonyl)-3-benzyloxycarboxyamido-2-azetidinone, is known. Chem. Pharm. Bull. 32: 2646–2659 (1984). The protecting group of the nitrogen bonded to C-3 is removed by hydrogenolysis to the corresponding free amine. An appropriate substituted tartaric acid enantiomer is added such as (+)-di-p-toluoyl-D-tartaric acid and reaction conditions altered to facilitate precipitation of the appropriate azetidinone enantiomer salt. The tartaric acid is removed by treating the compound with inorganic base such as sodium bicarbonate to obtain the C-3 free amino azetidinone which is then used as a starting material in the processes represented by Charts 1 and 2.

The compounds of Formula I have broad spectrum antimicrobial activity. They are useful as surface sterilants and as additives to products where microbial populations are sought to be limited, e.g., animal feed.

The compounds of Formula I are also effective for treating bacterial infections in mammals, including humans.

Various compositions of the present invention are presented for administration to humans and animals in unit dosage forms, such as tablets, capsules, pills, powders, granules, sterile parenteral solutions or suspensions, eye drops, solutions or suspensions, and water-in-oil emulsions containing suitable quantities of compounds of Formula I.

For parenteral administration, fluid unit dosage forms are prepared utilizing the compound and a sterile vehicle, water beng preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compounds of Formula I may also be administered in a carrier suitable for topical administration, such carriers include creams, ointments, lotions, pastes, jellies, sprays, aerosols, bath oils, or other pharmaceutical carriers which accomplish direct contact between the compound and the surface of the skin area to be treated. In general pharmaceutical preparations may comprise from about 0.01% to about 10%, and preferably from about 0.1% to about 5% by w/w of the active compound in the suitable suitable carrier.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate. These rectal suppositories can weigh from about 1 to 2.5 gm.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampoules, vials, aerosols with metered discharges, segregated multiples of any of the foregoing, and other forms as herein described.

An effective quantity of the compound is employed in treatment. The dosage of the compound for treatment depends on many factors that are well known to those skilled in the art. They include for example, the route of administration and the potency of the particular compound. A dosage schedule for humans having an average weight of 70 kg is from about 50 to about 3000 mg of compound in a single dose, administered parenterally or in the compositions of this invention, are effective for treating bacterial infections. More specifically, the single dose is from about 100 mg to 2000 mg of compound. The rectal dose is from about 100 mg to about 4000 mg in a single dose. More specifically, the single dose is from about 100 mg to about 2000 mg of compound. It is expected that the dosages can be given one to four times per day.

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

The parenthetical numbers following the compounds of the preparations and examples below refer to the generic compounds described in Charts 1 and 2.

Preparation 1; provides methods for placing various substituted silyl groups ($B_2$) on compound (1), cis-($\pm$)-4-methoxycarbonyl-3-[[(phenylmethoxy)carbonyl]amino]-2-azetidinone.

Preparation 1a; cis-($\pm$)-1-(t-Butyldimethyl)silyl-4-methoxycarbonyl-3-[[(phenylmethoxy)carbonyl]amino]-2-azetidinone (2).

To a solution of cis-($\pm$)-4-methoxycarbonyl-3-[[(phenylmethoxy)carbonyl]amino]-2-azetidinone (1), (J. of Org. Chem, 47: 2765–2767, 1982), (56.1 g, 0.2 mol), triethylamine (26.5 g, 0.26 mol) and 4-dimethylaminopyridine (3.3 g, 0.027 mol) in 300 ml of anhydrous dimethylformamide at 0° C., t-butyldimethylsilyl chloride (33.4 g, 0.22 mol) is added with stirring. After 30 minutes the reaction temperature is warmed to room temperature, at which temperature it is stirred for 3 hours. The precipitated solid is filtered and the filtrate solution is concentrated under reduced pressure. The residue is dissolved in ethyl acetate, washed with water, dried over anhydrous sodium sulfate, concentrated under reduced pressure to obtain the title compound (2). The crude solid product is used directly for the next step without any further purification.

Melting point: 115°–117° C.

$^1$H-NMR ($\delta$, CDCl$_3$): 7.33; 5.39; 5.1; 4.26; 3.7; 0.9; 0.35; 0.25.

Preparation 1b; cis-($\pm$)-1-(t-Butyldiphenyl)silyl-4-(methoxycarbonyl)-3-[[(phenylmethoxy)carbonyl]amino]-2-azetidinone (2)

A mixture of 1.10 g (4 mmol) of cis-($\pm$)-4-methoxycarbonyl-3-[[(phenylmethoxy)carbonyl]amino]-2-azetidinone (1) 680 mg (16 mmol) of imidazole and 1.31 g (4.8 mmol) of t-butyldiphenylsilyl chloride in 7 ml of dimethyl formamide is kept at room temperature for 2.5 days. The solution is concentrated under vacuum. The residue is dissolved in methylene dichloride and washed several times with water. The organic layer is dried and evaporated. Chromatography over 40 g of silica gel (Skellysolve-B-ethyl acetate, 4:1) gives the title compound.

$^{13}$C NMR (Me$_2$CO-d$_6$)$\delta$29.2; 51.3; 58.4; 61.5; 66.6; 127.8–136.2; 156, 169.8, 171.1; FAB mass spectrum of [M·+H]$^+$ calcd for C$_{29}$H$_{33}$N$_2$SiO$_5$: 517.2159. Found: 517.2153.

Preparation 1c; cis-($\pm$)-1-[(Triisopropyl)silyl]-4-methoxycarbonyl-3-[[(phenylmethoxy)-carbonyl]amino]-2-azetidinone A solution of 1.10 g (4.0 mmol) of cis-($\pm$)-4-(methoxycarbonyl)-3-[[(phenylmethoxy)carbonyl]amino]-2-azetidinone (1) 0.7 ml (5 mmol) of triethylamine, and 845 mg (4.4 mmol) of triisopropylsilyl chloride in 10 ml of tetrahydrofuran is maintained at ambient temperature for 2.5 days. The reaction mixture is washed successively, diluted with methylene dichloride and with dilute hydrochloric acid, water and potassium bicarbonate solution. After drying over sodium sulfate, the solution is evaporated to yield a crude product. The crude product is purified by chromatography over 40 g of silica gel (Skellysolve-B ethyl acetate, 4:1) to yield the title compound which forms a crystalline mass.

$^{13}$C NMR (Me$_2$CO-d$_6$)δ11.7; 17.7; 51.8; 58.2; 62.5; 66.6; 128.0, 128.5, 137; 170.8, 172; FAB mass spectrum of [M·+K]$^+$ calcd for C$_{22}$H$_{34}$N$_2$O$_5$SiK: 473.1874. Found: 473.1892.

Preparation 2; cis-(±)-1-t-(Butyldimethyl)silyl-4-hydroxymethyl-3-[[(phenylmethoxy)carbonyl]amino]-2-azetidinone (3).

Lithium borohydride (1.47 g) is added with stirring to a solution of cis-(±)-1-t-(butyldimethyl)silyl-4-methoxycarbonyl-3-[[2-(phenylmethoxy)carbonyl]amino]-2-azetidinone (2), (6.907 g, 17.5 mmol) in 50 ml of anhydrous tetrahydrofuran at 0° C. The reaction mixture is stirred at 0° C. for 4 hours and then is quenched by adding acetic acid (16 ml) dissolved in 50 ml ethyl acetate followed by an aqueous sodium bicarbonate solution. The organic layer is washed with brine, dried over anhydrous sodium sulfate and concentrated under reduced pressure to obtain a viscous residue. This crude product is passed through a silica gel column eluted with hexane/ethyl acetate (2:1), to afford the title product (3).

$^1$H-NMR (δ, CDCl$_3$): 7.4; 6.05; 5.25; 3.85; 2.45; 3.85; 2.45; 0.9; 0.35; 0.25.

Preparation 3

Compounds (4) having alternative blocking groups, B$_1$, are useful for preparing carbonate azetidines. The procedures for making these intermediates are described below.

Preparation 3a; cis-(±)-1-(t-Butyldimethyl)silyl-3-[[(9-fluorenylmethoxy)carbonyl]amino]-4-hydroxymethyl-2-azetidinone (4)

A solution of cis-(±)-1-(t-butyldimethyl)silyl-4-hydroxymethyl-3-[[(phenylmethoxy)carbonyl]amino]-2-azetidinone (3), (5.0 g, 13.7 mmol) in 50 ml of methanol, containing 2.5 g of palladium-black is stirred under one atmosphere of hydrogen gas at room temperature. Hydrogenolysis is complete in 40 minutes. Toluene (10 ml) is added to the mixture and stirred for 5 minutes. The catalyst is removed by filtration and washed with methanol. The filtrate is concentrated under reduced pressure to obtain the cis-(±)-3-amino-1-t-(butyldimethyl)silyl-4-hydroxymethyl-2-azetidinone.

One g (2.74 mmol) of cis-(±)-3-amino-1-(t-butyldimethyl)silyl-4-hydroxymethyl-2-azetidinone in 15 ml of methanol is reduced over 250 mg of Pd. The catalyst is removed by filtration and the solvent evaporated. The residue is dissolved in 15 ml of ether and 284 mg of 9-fluorenylmethyl chloroformate is added. A solution of 76 mg of potassium carbonate in 5 ml of water is added and the mixture vigorously stirred for 15 minutes. The organic layer is separated, dried and evaporated. The residue is chromatographed over 40 g of silica gel eluted with Skellysolve-B/ethyl acetate (3:1) to afford the title compound (4).

$^{13}$C NMR (Me$_2$SO-d$_6$)δ-2.7, —2.0; 26.0; 46.6; 56.7, 59; 60.9; 66.1; 119.1, 125.1, 126.9, 127.5, 140.8, 143.7; 155.7, 172.6; FAB exact mass of [M·+H]$^+$ calcd for C$_{25}$H$_{32}$N$_2$O$_4$Si: 453.2209. Found: 453.2225.

Preparation 3b; cis-(±)-1-(t-Butyldimethyl)silyl-3-[(t-butoxycarbonyl)amino]-4-(hydroxymethyl)-2-azetidinone (3) cis-(±)-4-(Methoxycarbonyl)-3-[[(phenylmethoxy)carbonyl]-amino]-2-azetidinone (1) (1.31 g, 9.1 mmol) and 600 mg of Pd-black in 15 ml of tetrahydrofuran is stirred under an atmosphere of hydrogen for 2 hours. The catalyst is removed by filtration and the solvent evaporated to leave 3-amino-4-(methoxycarbonyl)-2-azetidinone as a residue. This amine is dissolved in 15 ml of methylene dichloride and 1.99 g (9.1 mmol) of di-t-butyl-dicarbonate is added. After standing at room temperature for 3 days, the solution is concentrated under vacuum. Chromatography over 40 g of silica gel eluted with chloroform/methanol, (20:1) gives cis-(±)-3-[(t-butoxycarbonyl)amino]-4-methoxycarbonyl)-2-azetidinone.

$^{13}$C NMR (Me$_2$CO$_2$-d$_6$)δ28.4; 52.3; 56.2; 63.1; 76; FAB exact mass of [M·+K]$^+$ calcd. for C$_{10}$H$_{16}$KN$_2$O$_5$: 283.0696. Found: 283.0696.

To a solution of 1.46 g (0.6 mmol) of the above ester in 20 ml of methylene dichloride is added 707 mg (0.7 mmol) of triethylamine and 1.05 g of t-butyldimethylsilyl chloride. After standing overnight at ambient temperature, the reaction mixture is washed successively with dilute acid and water. The solution is dried and concentrated. Chromatography over 40 g of silica gel eluted with Skellysolve-B/ethylacetate, (3:1) affords cis-(±)-1-(t-butyldiphenyl)silyl-4-methoxycarbonyl)-3-[[(phenylmethoxy)carbonyl]-amino]-2-azetidinone. The title compound may be obtained by reducing the C-4 methoxycarbonyl to hydroxymethyl using either sodium borohydride, or lithium aluminum hydride as described in Preparation 2.

Preparation 4; cis-(±)-1-(t-Butyldimethyl)silyl-4-[(methoxycarbonyl)oxymethyl]-3-[[(phenylmethoxy)carbonyl]amino]-2-azetidinone (6).

Method A. Methyl chloroformate (2.0 ml, 25.8 mmol) is added dropwise while cooling in an ice bath to a solution of 1.092 g (3 mmol) of cis-(±)-1-(t-butyldimethyl)silyl-4-hydroxymethyl-3-[[(phenylmethoxy)carbonyl]amino]-2-azetidinone (3) in 25 ml of methylene dichloride and 1.6 ml of pyridine. When the addition is complete the bath is removed and the reaction is stirred at ambient temperature for 1 hour. The reaction mixture is diluted with methylene dichloride and washed successively with dilute acid, water, and potassium bicarbonate solution. The residue obtained on evaporation of the solvent is chromatographed over 40 g of silica gel eluted with Skellysolve-B/ethyl acetate (4:1). Fractions are combined on the basis of their thin layer chromatography profile to give the title compound (6).

$^{13}$C NMR (Me$_2$CO-d$_6$)δ-1.9, —1.7; 18.2, 25.9. 54.3. 54.6, 60.3; 66.5; 67.5, 127.9, 128.5, 137, 155; 172; FAB exact mass of [M·+H]$^+$ calcd for C$_{20}$H$_{31}$N$_2$O$_6$Si: 423.1951. Found: 423.1938.

In a similar manner by using the appropriate reactants and procedures essentially as described in preparations 1 through 4A the following corresponding compounds may be formed.

cis-(±)-1-(t-Butyldimethyl)silyl-4-[(phenoxycarbonyl)oxymethyl]-3-[[(phenylmethoxy)carbonyl]amino]-2-azetidinone $^{13}$C NMR (Me$_2$CO-d$_6$)δ-2.69–2.55; 18.09; 25.81; 54.22; 59.88; 66.88, 67.70; 115.35, 119.45, 120.87, 126.12, 127.76, 128.29, 129.45, 136.41,; 151.09, 157.14, 172.17. FAB exact mass of [M·+H]$^+$ calcd for C$_{25}$H$_{33}$N$_2$O$_6$S: 485.2108. Found: 485.2108.

cis-(±)-1-(t-Butyldimethyl)silyl-4-[(chloroethoxycarbonyl)oxymethyl]-3-[[(phenylmethoxy)carbonyl]amino]-2-azetidinone $^{13}$C NMR (Me$_2$CO-d$_6$)δ —1.8, —1.7, 25.9, 42.0, 54.3, 60.4, 66.6, 67.8, 128–137. FAB exact mass of [M·+H]$^+$ calcd for C$_{21}$H$_{31}$ClN$_2$O$_6$Si: 471.1718. Found: 471.1707.

cis-(±)-1-(t-Butyldimethyl)silyl-4-[(i-propoxycarbonyl)oxymethyl]-3-[[(phenylmethoxy)carbonyl]amino]-2-azetidinone.

$^{13}$C NMR (Me$_2$CO-d$_6$)δ —2.6, —2.4, 18.0, 21.1, 25.8, 25.9, 54.1, 59.9, 66.5, 71.7, 127.6–136.5, 154.0, 155.7, 171.7. FAB exact mass of [M·+H]$^+$ calcd for C$_{22}$H$_{35}$N$_2$O$_6$Si: 451.2264. Found: 451.2273.

cis-(±)-1-(t-Butyldimethyl)silyl-4-[(methoxyethoxycarbonyl)oxymethyl]-3-[[(phenylmethoxy)carbonyl]amino]-2-azetidinone $^{13}$C NMR (Me$_2$CO-d$_6$)δ —1.54; 18.33; 25.95; 54.36; 60.46; 65; 66.61, 67.25, 67.57, 70.25; 128.10, 128.63. FAB exact mass of [M·+H]$^+$ calcd for C$_{22}$H$_{35}$N$_2$O$_7$Si: 467.2213. Found: 467.2208.

Method B. Phosgene in toluene (0.87 ml of a 1.26M solution of phosgene in toluene) (1.10 mmol) is added dropwise while stirring in an ice bath to a solution of 58 mg (0.58 mmol) of triethylamine and 200 mg (0.55 mmol) of cis-(±)-3-amino-1-(t-Butyldimethyl)silyl-4-hydroxymethyl-2-azetidinone (4) is 5 ml of tetrahydrofuran. After stirring for a few minutes, thin layer chromatography on silica gel (Skellysolve B ethyl acetate, 2:1) will show the presence of a faster spot and disappearance of the starting alcohol (4). This new product need not be isolated. It is probably the chloroformate ester, cis(±)-1-(t-butyldimethyl)silyl-4-[(chlorocarbonyl)oxymethyl]-3-[[(phenylmethoxy)-carbonyl]amino]-2-azetidinone (5). The reaction mixture is placed under vacuum to remove the excess phosgene. A solution of 132 mg (2.2 mmol) of methanol in tetrahydrofuran is added followed by 58 mg (0.58 mmol) of triethylamine. The reaction mixture is worked up as described above and chromatographed over 35 g of silica gel (Skellysolve B ethyl acetate, 4:1) to afford the title carbonate (6), identical with that prepared by Method A.

In a similar manner by using the appropriate reactants and procedures essentially as described in Preparations 1 through 4B the following corresponding compound may be formed.

cis-(±)-1-(t-Butyldimethyl)silyl-4-[(formylaminoethoxycarbonyl)oxymethyl]-3-[[(phenylmethoxy)carbonyl]amino]-2-azetidinone $^{13}$C NMR (Me$_2$CO-d$_6$)δ —1.50, —1.41; 18.37; 25.98; 36.86; 54.35; 60.54; 66.68, 66.83, 67.45; 128.06, 128.64; 156, 161.32. FAB exact mass of [M·+H]$^+$ calcd for C$_{22}$H$_{34}$N$_3$O$_7$Si: 480.2166. Found: 480.2164.

cis-(±)-1-(t-Butyldimethyl)silyl-4-[(t-butoxycarbonylaminoethoxycarbonyl)oxymethyl]-3-[[(phenylmethoxy)carbonyl]amino]-2-azetidinone $^{13}$C NMR (Me$_2$CO-d$_6$)δ —1.3, —1.2, 19.1, 26.8, 28.9, 40.3, 55.0, 61.1, 67.8, 68.1, 128.8–137.7, 155.5, 156.5, 172.6. FAB exact mass of [M·+H]$^+$ calcd for C$_{26}$H$_{42}$N$_3$O$_8$Si: 552.2741. Found: 552.2636.

cis-(±)-1-(t-Butyldimethyl)silyl-4-[(carbamoyloxyethoxycarboyl)oxymethyl]-3-[[(phenylmethoxy)carbonyl]amino]-2-azetidinone $^{13}$C NMR (Me$_2$CO-d$_6$)δ —2.2, —2.0, 18.1, 25.8, 54.1, 60.1, 62.0, 66.5, 67.3, 127.9–128.4, 154.6, 156.06, 156.8, 172.0.

Preparation 5; cis-(±)-3-[2-(2-t-Butoxycarbonylamino-4-thiazolyl)(Z)-2-(t-butoxycarbonyl)methoxyiminoacetamido]-1-(t-butyldimethyl)silyl-4-[(methoxycarbonyl)oxymethyl]-2-azetidinone (8).

A mixture of 1.01 g (2.37 mmol) of cis-(±)-1-(t-butyldimethyl)silyl-4-[(methoxycarbonyl)oxymethyl]-3-[[(phenylmethoxy)carbonyl]amino]-2-azetidinone (6) and 500 mg of Pd in 20 ml of tetrahydrofuran is stirred under nitrogen for 1.25 hours. Thin layer chromatography on silica gel (chloroform-methanol, 10:1) shows the absence of carbonate (6) and the appearance of a more polar, ninhydrin positive spot, i.e., cis-(±)-3-amino-1-(t-butyldimethyl)silyl-4-[(methoxycarbonyl)oxymethyl]-2-azetidinone (7). The catalyst is removed by filtration. To the solution of amine (7) in tetrahydrofuran is added 1.14 g (2.85 mmol) of 2-(2-t-butoxycarbonylaminothiazole-4-yl)-2-(t-butoxycarbonyl)methoxyiminoacetic acid, 587 mg (2.85 mmol) of dicyclohexylcarbodiimide and 384 mg of 1-hydroxybenzotriazole. The mixture is stirred at ambient temperature for 17 hours. The solids are removed by filtration and discarded. The filtrate is evaporated under vacuum. The residue is dissolved in methylene dichloride and the solution washed with dilute acid and base. The organic solution is dried and concentrated. The residue is chromatographed over 40 g of silica gel using Skellysolve-B/ethyl acetate, 4:1, for elution. The major fraction is the title compound (8).

$^{13}$C NMR (Me$_2$CO-d$_6$)δ0, 0.2, 19, 26.5, 28.2, 54.9, 55.4, 58.8, 69.7, 71.9, 82.4, 114.8, 142, 151, 154, 156, 161, 163, 170, 172; FAB mass spectrum for [M·+H]$^+$ calcd for C$_{28}$H$_{46}$N$_5$O$_{10}$SSi: 672.2734. Found: 672.2748.

In a similar manner using the appropriate reactants and the procedure essentially as described in Preparation 5a, the following corresponding compounds may be formed.

cis-(±)-1-(t-Butyldimethyl)silyl-4-[(methoxycarbonyl)oxymethyl]-3-[2-(2-triphenylmethylamino-4-thiazolyl)-(Z)-2-methoxyimino acetamido]-2-azetidinone.

$^{13}$C NMR (CDCl$_3$)δ 2.4; 18.2; 25.8; 54.1, 54.7, 57.5; 62.6; 67.1; 112.0, 140.6, 162.5; 127–129, 142.9; 154.9, 168.4, 170.9; FAB exact mass of [M·+H]$^+$ calcd for C$_{37}$H$_{44}$N$_5$O$_6$SSi: 714.2781. Found: 714.2776.

cis-(±)-1-(t-Butyldimethyl)silyl-4-[(methoxycarbonyl)oxymethyl]-3-[2-(2-amino-4-thiazolyl)-(Z)-2-[1-methyl-1-(t-butoxycarbonyl)]ethoxyiminoacetamido]-2-azetidinone $^{13}$C NMR (CD$_3$OD)δ 2.20, 2.39; 19.20; 24, 33, 25.89; 26.64; 28.28; 55.53, 55.88; 58.76; 68.96; 82.96, 84.04; 111.25, 143.34, 165.02; 149.99; 156.59; 170.96, 173.35, 174.96.

cis-(±)-1-(t-Butyldimethylsilyl)-3-[D(−)-α-(4-ethyl-2,3-dioxo-1-piperizinocarbonylamino)-phenylacetamido]-4-[(methoxycarbonyl)oxymethyl]-2-azetidinone $^{13}$C NMR (Me$_2$CO-d$_6$)δ —1.65; 11.71; 18.25; 25.87; 28.23; 40.87; 42.13, 43.46; 54.33, 54.63; 58.11, 58.66; 67.52; 127.34–128.90, 138.19; 152.54, 155–156, 161, 171.16, 172.

cis-(±)-3-[2-(2-t-Butoxycarbonylamino-4-thiazolyl)-(Z)-2-(t-butoxycarbonyl)methoxyiminoacetamido]-1-(t-butyldimethyl)silyl-4-[phenoxycarbonyl)oxymethyl]-2-azetidinone $^{13}$C NMR (Me$_2$CO-d$_6$)δ —1.82, —1.65; 18.38; 25.92; 27.59; 54.24; 58.28; 69.51, 71.39; 81.87; 114–151; 152.8, 153.5, 160.3, 162.2, 169.4, 170.9.

cis-(±)-3[2-(2-t-Butoxycarbonylamino-4-thiazolyl)-(Z)-2-(t-butoxycarbonyl)methoxyiminoacetamido]-1-(t-butyldimethyl)silyl-4-[(methoxyethoxycarbonyl)oxymethyl]-2-azetidinone $^{13}$C NMR (Me$_2$CO-d$_6$)δ —1.59, —1.44; 18.31; 25.94; 27.66; 54.38; 58.34; 67.42, 69.28, 70.20, 71.47; 81.92; 114, 142. FAB exact mass of [M·+H]+ calcd for C$_{20}$H$_{50}$N$_5$O$_{11}$Si: 716.2997. Found: 716.3006.

cis-(±)-3-[2-(2-t-Butoxycarbonylamino-4-thiazolyl)-(Z)-2-(t-butoxycarbonyl)methoxyiminoacetamido]-1-(t-butyldimethyl)silyl-4-[(formylaminoethoxycarbonyl)oxymethyl]-2-azetidinone $^{13}$C NMR (Me$_2$CO-d$_6$)δ —2.00, —1.84; 18.15; 25.82; 27.58; 36.68; 54.22; 58.10; 66.69, 68.93, 71.32; 81.79; 114.32, 141.84, 154.93, 150.57; 152.79, 160.31, 161.67, 162.26, 169.28, 170.94. FAB exact mass of [M·+H]+ calcd for C$_{30}$H$_{49}$N$_6$O$_{11}$SSi: 729.2949. Found: 729.2945.

cis-(±)-3-[1-(2-t-Butoxycarbonylamino-4-thiazolyl)-(Z)-2-(t-butoxycarbonyl)methoxyiminoacetamido]-1-(t-butyldimethyl)silyl-4-[(chloroethoxycarbonyl)oxymethyl]-2-azetidinone $^{13}$C NMR (Me$_2$CO-d$_6$) δ—1.7, —1.5, 18.3, 26.0, 41.9, 54.3, 58.3, 68.0, 69.0, 71.5, 81.9, 114.4, 169. FAB exact mass of [M·+H]+ calcd for C$_{29}$H$_{27}$ClN$_5$O$_{10}$SiS: 720.2501. Found: 720.2503.

cis-(±)-3-[2-(2-t-butoxycarbonylamino-4-thiazolyl)-(Z)-2-(t-butoxycarbonyl)methoxyiminoacetamido]-1-(t-butyldimethyl)silyl-4-[(t-butoxycarbonylaminoethoxycarbonyl)oxymethyl]-2-azetidinone.

$^{13}$C NMR (Me$_2$CO-d$_6$) δ—2.0, —1.9, 18.4, 25.8, 27.6, 27.9, 39.4, 54.2, 58.1, 67.1, 69.1, 71.3, 81.8, 114.3, 115.6, 152.8, 155.1, 160.3, 162, 169.4, 170.9. FAB exact mass of [M·+H]+ calcd for C$_{34}$H$_{57}$N$_6$O$_{12}$SiS: 801.3524. Found: 801.3528.

cis-(±)-3-[2-(2-t-Butoxycarbonylamino-4-thiazolyl)-(Z)-2-(t-butoxycarbonyl)methoxyiminoacetamido]-1-(t-butyldimethyl)silyl-4-[(carbomoyloxyethoxycarbonyl)oxymethyl]-2-azetidinone.

$^{13}$C NMR (Me$_2$CO-d$_6$) δ—1.7, 1.6, 18.3, 25.9, 27.7, 54.3, 58.2, 62.0, 66.7, 69.2, 71.4, 81.9, 114.6, 162.3, 171.0. FAB exact mass of [M·+H]+ calcd for C$_{30}$H$_{44}$N$_6$O$_{12}$SiS: 745.2898. Found: 745.2899.

cis-(±)-3-[2-(2-t-Butoxycarbonylamino-4-thiazolyl)-(Z)-2-(t-butoxycarbonyl)methoxyiminoacetamido]-1-(t-butyldimethyl)silyl-4-[(i-propoxycarbonyl)oxymethyl]-2-azetidinone.

$^{13}$C NMR (Me$_2$CO-d$_6$) δ—2.0, 20.2, 25.9, 27.7, 54.4, 58.2, 69.0, 71.4, 72.2, 81.8, 114.2, 142.0, 152.8, 154.7, 163.2, 169.3, 170.4. FAB exact mass of [M·+H]+ calcd for C$_{30}$H$_{50}$N$_5$O$_{10}$SiS: 700.3047. Found: 700.3031.

Preparation 6; cis-(±)-1-(t-Butyldimethyl)silyl-4-[(methoxycarbonyl)oxymethyl]-3-[2-(2-triphenylmethylamino-4-thiazolyl)-(Z)-2-[1-methyl-1-(t-butoxycarbonylethoxy)]iminoacetamido]-2-azetidinone (8)

Triphenylmethylchloromethane (742 mg, 2.66 mmol) is added, while stirring in an ice bath, to a solution of 1.45 g (2.42 mmol) of cis-(±)-1-(t-butyldimethyl)silyl-4-[(methoxycarbonyl)oxymethyl]-3-[2-(2-amino-4-thiazolyl)-(Z)-2-[1-methyl-1-(t-butoxycarbonyl)]ethoxyiminoacetamido]-2-azetidinone, from preparation 5, compound (b), in 10 ml of pyridine. After 2 hours the pyridine is evaporated in vacuo. The residue is partitioned between methylene dichloride and dilute acid. The organic layer is dried and concentrated. Chromatography of the residue over 40 g of silica gel (ethyl acetate/Skellysolve-B 1:2) affords the title compound (8).

$^{13}$C NMR (MeOH-4d) δ2.35, 2.55; 19.26; 24.34; 26.66; 28.26; 55.53, 55.88; 58.83; 69.12; 70; 84.11; 111.74; 128-130, 141, 144.85; 150, 156, 165, 170, 174, 175.

EXAMPLE 1 cis-(±)-3-[2-(2-Amino-4-thiazolyl)-(Z)-2-carboxymethoxyiminoacetamido]-4-[(methoxycarbonyl)oxymethyl]-2-oxo-1-azetidinesulfonic Acid, Potassium Salt Two equivalents of dimethylformamide-sulfur trioxide reagent (4.2 ml of 1.0M solution, 4.2 mmol) are added to a solution of 1.410 g (2.10 mmol) of carbonate cis-(±)-3-[2-(2-t-Butoxycarbonylamino-4-thiazolyl)-(Z)-2-(t-butoxycarbonyl)methoxyiminoacetamido]-1-(t-butyldimethyl)silyl-4-[(methoxycarbonyl)oxymethyl]-2-azetidinone (8) from Preparation 5, dissolved in 5 ml of dimethylformamide. After 3 hours at ambient temperature thin layer chromatography (chloroform-methanol, 2:1)shows the absence of carbonate (8). The reaction mixture is poured into 500 ml of 0.5 monobasic potassium biphosphate solution. This solution is extracted twice with 100 ml portions of methylene dichloride. Tetrabutylammonium bisulfate (1.425 g) is added to the methylene dichloride solution. The solution is washed with 50 ml of H$_2$O, dried, and concentrated. A solid residue remains. This material is dissolved in 12 ml of methylene dichloride. Trifluoroacetic acid (15 ml) is added dropwise while stirring in an ice bath. Following the addition of the acid, the reaction mixture is stirred at ambient temperature for 0.5 hour. The mixture is concentrated under vacuum. The residue is triturated with 50 ml of anhydrous ether. The precipitate is collected by filtration and dried. This solid is dissolved in 30 ml of water and clarified by filtration. The filtrate is passed through a column of 30 ml of Dowex 50 (K+) and the column is washed with water. Fractions containing the above titled salt are combined and passed through a column of 150 ml of HP-20 resin. The column is eluted with 450 ml of water, followed by 300 ml of 10% aqueous acetone and 300 ml of 20% aqueous acetone. Fractions are monitored by dipping 12.5 mm paper discs and spotting on an agar tray seeded with Klebsiella pneumoniae. Fractions are combined on the basis of the sizes of their zones of inhibition. Fractions are lyophilized.

$^{13}$C NMR (D$_2$O ) δ56.8, 57.7, 58.8; 65.5; 74.2; 114.4, 142; 157, 166, 169. FAB exact mass of [M·+K]+ Calcd for C$_{13}$H$_{14}$K$_2$N$_5$O$_{11}$S$_2$: 557.9405. Found: 557.9410.

In a similar manner using the appropriate reactants and the procedures essentially as described in Examples 1, the following compounds are formed.

cis-(±)-3-[2-(2-Amino-4-thiazolyl)-2-(1-methyl-1-carboxy)ethoxyiminoacetamido]-4-[(methoxycarbonyl)oxymethyl]-2-oxo-1-azetidinesulfonic acid, potassium salt $^{13}$C NMR (D$_2$O) δ23.99; 56.45; 57.25; 58.55; 65.12; 85.47; 112.50, 143.38, 162; 148.45; 156.56, 164.66, 171.67, 178.11.

cis-(±)-3-[2-(2-Amino-4-thiazolyl)-(Z)-2-[carboxymethoxyiminoacetamido]-4-[(phenoxycarbonyl)oxymethyl]-2-oxo-1-azetidinesulfonic acid, potassium salt $^{13}$C NMR (DMSO-d$_6$) δ55.4, 55.5; 65.4; 70; 121.1, 126.0, 129.5.

cis-(±)-3-[2-(2-Amino-4-thiazolyl)-(Z)-2-carboxymethoxyiminoacetamido]-4-[(methoxyethoxycarbonyl)oxymethyl]-2-oxo-1-azetidinesulfonic acid, potassium salt $^{13}$C NMR (DMSO-d$_6$) δ55.71, 58.03; 65.17, 66.68, 69.50, 74; other lines obscured. FAB exact mass calcd for (M·+K)+ C$_{15}$H$_{18}$N$_5$O$_{12}$S$_2$K$_2$: 601.9667. Found: 601.9678.

cis-(±)-3-[2-(2-Amino-4-thiazolyl)-(Z)-2-(carboxymethoxyimino)acetamido]-4-[(formylaminoethoxycarbonyl)oxymethyl]-2-oxo-1-azetidinesulfonic acid $^{13}$C NMR (DMSO-d$_6$) δ55.86, 56.22, 64.24, 65.05, 73.25, 119.15, 142.83, 154.88, 161.96, 168.34, 173.12. FAB mass spectrum shows [M·+K]$^+$ at m/z 615.

cis-(±)-3-[2-(2-Amino-4-thiazolyl)-(Z)-2-(carboxymethoxyiminoacetamido)]-4-[(chloroethoxycarbonyl)oxymethyl]-2-oxo-1-azetidinesulfonic acid.

$^{13}$C NMR (Me$_2$SO-d$_6$) δ55.4, 55.8, 64.8, 67.5, 67.7, 71.2, 109.7, 111.4, 119.2, 124.7, 133.9, 145.9, 160.1, 161.6, 170.5. FAB exact mass of [M·+H]$^{30}$ calcd for C$_{14}$H$_{17}$ClN$_5$O$_{11}$S$_2$: 530.0654. Found: 530.0074.

cis-(±)-3-[2-(2-Amino-4-thiazolyl)-(Z)-2-(carboxymethoxyiminoacetamido)]-4-[(aminoethoxycarbonyl)oxymethyl]-2-oxo-1-azetidinesulfonic acid.

$^{13}$C NMR (Me$_2$SO-d$_6$) δ38.2, 55.9, 64.3, 65.6, 70.8, 110.3, 142.2, 146.5, 149.9, 153.8, 162.0, 162.2, 168.6, 171.0. FAB exact mass of [M·+H]$^+$ calcd for C$_{14}$H$_{19}$N$_6$O$_{11}$S$_2$: 511.0553. Found: 511.0577.

cis-(±)-3-[2-(2-Amino-4-thiazolyl)-(Z)-2-(carboxymethyoxyiminoacetamido)]-4-[(carbamoyloxyethoxycarbonyl)oxomethyl]-2-oxo-1-azetidinesulfonic acid.

$^{13}$C NMR (Me$_2$SO-d$_6$) δ55.7, 55.8, 61.5, 64.8, 66.5, 71.2, 111.4, 134.9, 146.5, 154.2, 156.5, 160.4, 161.7, 169.8, 170.6. FAB exact mass of [M·+H]$^+$ calcd for C$_{15}$H$_{19}$N$_6$O$_{13}$S$_2$: 555.0451. Found: 555.0475.

cis-(±)-3-[2-(2-Amino-4-thiazolyl)-(Z)-2-(carboxymethoxyiminoacetamido)]-4-[(i-propoxycarbonyl)oxymethyl]-2-oxo-1-azetidinesulfonic acid.

$^{13}$C NMR (Me$_2$SO-d$_6$) δ21.6, 55.6, 55.8, 64.1, 70.9, 71.9. FAB exact mass of [M·+H]$^+$ calcd for C$_{15}$H$_{20}$N$_5$O$_{11}$S$_2$: 510.0601. Found: 510.0596.

EXAMPLE 2 cis-(±)-3-[2-(2-Amino-4-thiazolyl)-(Z)-2-methoxyiminoacetamido]-4-[(methoxycarbonyl)oxymethyl]-2-oxo-1-azetidinesulfonic Acid, Potassium Salt To a partial solution of 1.833 g (2.57 mmol) of cis-(±)-3-[2-(2-t-butoxycarbonylamino-4-thiazolyl)-(Z)-2-(t-butoxycarbonyl)methoxyiminoacetamido]-1-(t-butyldimethyl)silyl-4-[(methoxycarbonyl)oxymethyl]-2-azetidinone (8) from Preparation 5, in 6.3 ml of dimethylformamide is added 5.14 ml (5.14 mmol) of dimethylformamide-sulfur trioxide reagent. After 30 minutes thin layer chromatography (chloroform-methanol, 10:1) shows the absence of carbonate (8). The reaction mixture is poured into 480 ml of 0.5M monobasic potassium biphosphate solution. Tetrabutylammonium bisulfate (1.75 g, 5.15 mmol) is added. The aqueous solution is extracted four times with 125 ml of methylene dichloride. The combined extracts are washed with water, dried, and evaporated. The residue is dissolved in 36 ml of 70% formic acid. After 45 minutes at ambient temperature the solution is evaporated under vacuum. Water is added to the residue and the solvent is evaporated again. The residue is warmed for a few minutes with 38.5 ml of water. The solution is filtered to remove a small amount of gummy residue. The filtrate is passed through a column of 38.5 ml of Dowex 50 (K$^+$) resin. The column is washed in water. Fractions containing the title monobactam (Example 2) are refrigerated overnight, during which time crystals precipitate. These are collected and dried.

$^{13}$C NMR (Me$_2$SO-d$_6$) δ55.1, 55.1, 55.9; 63.4; 64.7; 111.0, 132.9, 160.1; 144.3; 154.9, 161.8, 170.4.

Additional amounts of Example 2 are obtained by passing the mother liquors from the filtration of crystals through a column of 190 ml of HP-20 resin. The resin is eluted with 570 ml of water followed by 380 ml portions of 10% aqueous acetone and 380 ml of 20% aqueous acetone. Fractions are monitored as described above, combined, and lyophilized.

In a similar manner using the appropriate reactants and the procedures essentially as described in Example 2, the following compound is formed.

cis-(±)-3-[D(-)-(α)-(4-Ethyl-2,3-dioxo-1-piperizinocarbonylamino)phenylacetamido]-4-[(methoxycarbonyl)oxymethyl]-2-oxo-1-azetidinesulfonic acid, potassium salt $^{13}$C NMR (D$_2$O) δ12.59; 42.05; 44.68, 44.83; 57.05; 58.01, 58.90, 59.08, 60.45; 65.67; 128.6–130.4.

EXAMPLE 3 cis-(+)-3-[2-(2-Amino-4-thiazolyl)-(Z)-2-carboxymethoxyiminoacetamido]-4-[(methoxycarbonyl)oxymethyl]-2-oxo-1-azetidinesulfonic Acid, Potassium Salt The optically active title compound is obtained by resolving the enantiomers of cis-(±)-3-benzyloxycarboxamido-4-methoxycarbonyl-1-(2,4-dimethoxybenzyl)-2-azetidinone. Chem. Pharm. Bull. 32: 2646–2659 (1984). To this racemic mixture (207.3 g, 0.48 mole) in 500 ml of tetrahydrofuran at room temperature is added 78.5 g of Palladium-black. The hydrogenolysis reaction is carried out under one atmosphere of hydrogen gas. Toluene (100 ml) is added to the reaction mixture and stirred for 15 minutes. The catalyst is removed by filtration and washed several times with tetrahydrofuran. The solvent is evaporated to yield cis-(±)-1-(2,4-dimethoxybenzyl)-4-methoxycarbonyl-3-amino-2-azetidinone.

The above amino azetidinone is dissolved in 3 liters of acetonitrile and (+)-di-p-toluoyl-D-tartaric acid (200 g, 0.5 mole) is added with stirring. The solution is warmed to dissolution and allowed to cool to room temperature. The solid precipitate is then collected by filtration and washed with ice-cold acetonitrile. The solid is recrystalized from 3 liters of acetonitrile to obtain the tartrate salt of cis-(+)-1-(2,4-dimethoxybenzyl)-4-methoxycarbonyl-3-amino-2-azetidinone.

The above salt is then dissolved in tetrahydrofuran (1 liter) and water (400 ml) at 0° C. Sodium bicarbonate (34.9 g, 0.41 mole) and benzylchloroformate (26.0 ml, 0.23 mole) are added with stirring. After one hour at 0° C., the reaction mixture is warmed to room temperature and stirred for 30 minutes. The reaction mixture is then concentrated under reduced pressure and the aqueous residue is diluted with ethyl acetate (3 liters) and water (1 liter). The organic layer is taken and the aqueous layer is rewashed with ethyl acetate (500 ml). The organic layers are combined and washed successively with 2% aqueous sodium bicarbonate, 1N HCl, brine, and 2% aqueous sodium bicarbonate (500 ml each). The organic layer is then dried over sodium sulfate and concentrated under reduced pressure. The resulting material is triturated with ether to obtain the desired enantiomer, cis-(+)-3-benzyloxycarboxyamido-4-methoxycarbonyl-1-(2,4-dimethoxybenzyl)-2-azetidinone. The above enantiomer is treated with ceric ammonium nitrate at 0° C. in acetonitrile to yield cis-(+)-4-methoxycarbonyl-2-oxo-3[[(phenylmethoxy)carbonyl]amino]-1-azetidinone.

The enantiomer is then reacted under the identical conditions described for the preparation of cis-(±)-3-[2-(2-amino-4-thiazolyl)-(Z)-2-carboxymethoxyiminoacetamido]-4-[(methoxycarbonyl)oxymethyl]-2-oxo-1-azetidinesulfonic acid, potassium salt beginning with Preparation 1 converting the 4-methoxycarbonyl-2-oxo-3-[[(phenylmethoxy)carbonyl]-amino]-1-azetidine (1) to 1-(t-butyldimethyl)silyl-3-[[2-(phenylmethoxy)carbonyl]-amino]-4-methoxycarbonyl-2-azetidinone (2) or other N-1 silyl substituted analog such as triisopropyl or t-butyldiphenyl silyl described above.

TABLE 1
ANTIMICROBIAL IN VITRO TESTING

| Organism Name | UC#[1] | Minimum Inhibitory Concentration (mcg/ml)[2] | |
| --- | --- | --- | --- |
| | | A | B |
| Enterobacter cloacae | 9381 | 128 | >64 |
| Enterobacter cloacae | 9382 | 0.5 | 1 |
| Klebsiella pneumoniae | 9383 | 0.5 | 16 |
| Klebsiella pneumoniae | 9384 | 0.125 | 0.25 |
| Escherichia coli | 9379 | <0.06 | 0.125 |
| Escherichia coli | 9380 | 1 | 1 |
| Staphylococcus aureus | 6675 | >128 | >64 |
| Staphylococcus aureus | 3665 | >128 | >64 |
| Staphylococcus aureus | 6685 | >128 | >64 |
| Streptococcus pyogenes | 152 | 8 | 0.5 |
| Streptococcus pneumoniae | 41 | 32 | 4 |
| Streptococcus faecalis | 694 | >128 | >64 |
| Escherichia coli | 311 | 0.25 | 0.5 |
| Klebsiella pneumoniae | 58 | 0.125 | 0.25 |
| Pseudomonas aeruginosa | 9191 | 16 | 32 |
| Pseudomonas aeruginosa | 6432 | 0.5 | >64 |
| Serratia marcescens | 6888 | 0.5 | 2 |
| Citrobacter freundii | 3507 | 0.25 | 0.5 |

[1] UC is a registered trademark of The Upjohn Company.
[2] Compound A is cis-($\pm$)-3-[2-(2-amino-4-thiazolyl)-(Z)-2-carboxymethoxy-iminoacetamido]-4-[(methoxycarbonyl)oxymethyl]2-oxo-1-azetidinesulfonic acid, potassium salt; and Compound B is cis-($\pm$)-3-[2-(2-amino-4-thiazolyl)-(Z)-2-methoxyiminoacetamido]-4-[(methoxycarbonyl)oxymethyl]-2-oxo-1-azetidinesulfonic acid, potassium salt.

FORMULAS

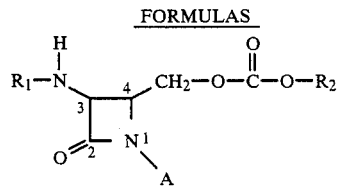

(I)

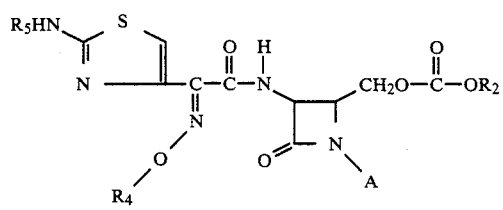

(II)

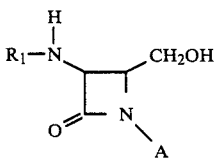

(III)

CHART 1

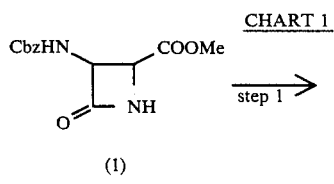

(1)

-continued CHART 1

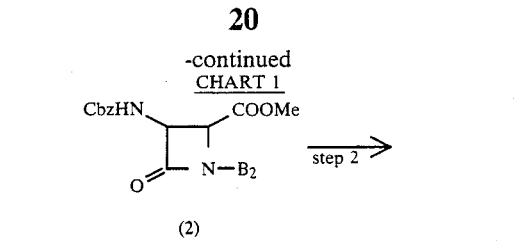

CHART 2

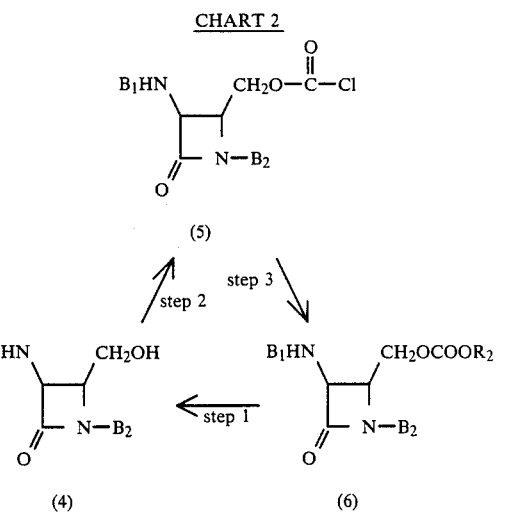

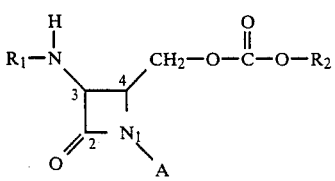

(9)

I claim:
1. A compound of the formula:

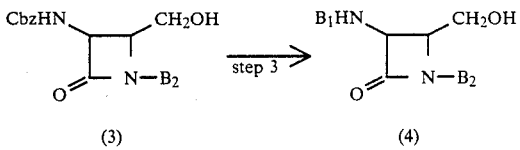

(I)

or a pharmaceutically acceptable salt thereof, wherein:
R₁ is an acyl group derived from a carboxylic acid;
A is sulfo;
R₂ is selected from the group consisting of:
  a. (C₁–C₈)alkyl;
  b. (C₂–C₈)alkenyl;
  c. (C₃–C₈)alkynyl;
  d. (C₃–C₈)cycloalkyl;
  e. (C₆–C₈)aryl;
  f. (C₆–C₁₂)aralkyl;
  g. heterocyclic radicals selected from the group consisting of 2- or 3-pyrrolyl, 2- or 3-furyl, 2- or 3-thienyl, 2- or 3-pyrrolidinyl, 2-, 3- or 4-pyridyl, N-oxido-2-, 3- or 4-pyridyl, 2-, 3-or 4-piperidinyl, 2-, 3- or 4-pyranyl, 2-, 3- or 4-thiopyranyl, pyrazinyl, 2-, 4- or 5-thiazolyl, 2-, 4- or 5-oxazolyl, 3-, 4- or 5-isothiazolyl, 3-, 4- or 5-isoxazolyl, 2-, 4- or 5-imidazolyl, 3-, 4- or 5-pyrazolyl, 3- or 4-pyridazinyl, 2-, 4- or 5-pyrimidinyl, piperazinyl, 4- or 5-(1,2,3-thiadiazolyl), 3- or 5-(1,2,4-thiadiazolyl), 1,3,4-thiadiazolyl, 1,2,5-thiadiazolyl, 4- or 5-(1,2,3-oxadiazolyl), 3- or 5-(1,2,4-oxadiazolyl), 1,3,4-oxadiazolyl, 1,2,5-oxadiazolyl, 1,2,3- or 1,2,4-triazolyl, 1H- or 2H-tetrazolyl, pyrido(2,3-d)pyrimidyl, benzopyranyl, 1,8-, 1,5-, 1,6-, 1,7-, 2,7- or 2,6-naphthyridyl, quinolyl, and thieno(2,3-b)pyridyl;
where each member of (a) through (g) may be substituted by 1 to 4 substituents selected from the group consisting of methoxy, hydroxy, halogen, nitro, and N(R₁₀)(R₁₁) wherein R₁₀ is hydrogen or alkyl (C₁–C₄) and R₁₁ is hydrogen, alkyl (C₁–C₄) or alkoxy (C₁–C₄) provided that when R₁₁ is alkoxy, R₁₀ must be hydrogen; and
  h. (CH₂)ₙCH₂X where n is 1 to 4 and X is —OR₃ where R₃ is selected from the group consisting of (C₂–C₄) alkyl, (C₂–C₃) alkoxyalkyl and (C₂–C₄) alkylcarbonyl or X is (C₂–C₄) alkylcarbonylamino.

2. A compound according to claim 1 wherein R₂ is selected from the group consisting of:
  a. (C₁–C₈) alkyl;
  b. (C₂–C₈) alkenyl;
  c. (C₃–C₈) alkynyl;
  d. (C₃–C₈) cycloalkyl;
  e. (C₆–C₈) aryl;
  f. (C₆–C₁₂) aralkyl; and
  g. heterocyclic radicals;
wherein each member of the group (a) through (g) may be substituted by 1 to 4 substituents selected from the group consisting of methoxy, hydroxy, nitro, halogen, and —N(R₁₀)(R₁₁) wherein R₁₀ is hydrogen or alkyl (C₁–C₄) and R₁₁ is hydrogen, alkyl (C₁–C₄) or alkoxy (C₁–C₄) provided that when R₁₁ is alkoxy, R₁₀ must be hydrogen.

3. A compound according to claim 1 wherein R₂ is (CH₂)ₙCH₂X.

4. A compound according to claim 1 wherein R₁ is

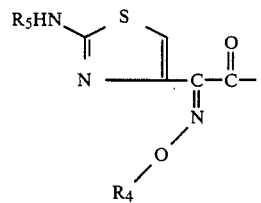

wherein R₄ is selected from the group consisting of: (C₁–C₄) alkyl; (C₂–C₃) alkenyl; (C₃–C₄) alkynyl; and substituted (C₁–C₄) alkyl such that the word substituted refers to 1 to 3 members of the following moieties, amino, azido, carboxy, chloro, bromo, cyano, fluoro, hydroxy, (C₂–C₄) alkoxycarbonyl, aminocarbonyl, (C₁–C₃) alkoxy and (C₁–C₃) alkylthio;
wherein R₅ is selected from the group consisting of: hydrogen, t-butoxycarbonyl, phenylmethoxycarbonyl, and triphenylmethyl; and,
wherein the substituted oxime is in the syn (Z) configuration.

5. A compound according to claim 4 selected from the group consisting of C-3 and C-4 cis isomers of:
  3-[2-(2-amino-4-thiazolyl)-(Z)-2-carboxymethoxyiminoacetamdio]-4-[(methoxycarbonyl)oxymethyl]-2-oxo-1-azetidinesulfonic acid and the potassium salt thereof;
  3-[2-amino-4-thiazolyl]-(Z)-2-methoxyiminoacetamido]-4-[(methoxycarbonyl)oxymethyl]-2-oxo-1-azetidinesulfonic acid and the potassium salt thereof;
  3-[2-(2-amino-4-thiazolyl)-(Z)-2-(1-methyl-1-carboxyethoxyimino)acetamido]-4-[(methoxycarbonyl)oxymethyl]-2-oxo-1-azetidinesulfonic acid and the potassium salt thereof;
  3-[2-(2-amino-4-thiazolyl)-(Z)-2-carboxymethoxyiminoacetamido]-4-[(phenoxycarbonyl)oxymethyl]-2-oxo-1-azetidinesulfonic acid and the potassium salt thereof;
  3-[2-(2-amino-4-thiazolyl)-(Z)-2-carboxymethoxyiminoacetamido]-4-[(methoxyethoxycarbonyl)oxymethyl]-2-oxo-1-azetidinesulfonic acid and the potassium salt thereof;
  3-[2-(2-amino-4-thiazolyl)-(Z)-2-(carboxymethoxyiminoacetamido)]-4-[(chloroethoxycarbonyl)oxymethyl]-2-oxo-1-azetidinesulfonic acid;
  3-[2-(2-amino-4-thiazolyl)-(Z)-2-(carboxymethoxyimino-acetamido)]-4-[(aminoethoxycarbonyloxymethyl]-2-oxo-2-azetidinesulfonic acid;
  3-[2-(2-amino-4-thiazolyl)-(Z)-2-(carboxymethoxyiminoacetamido)]-4-[(carbamoyloxyethoxycarbonyl)oxomethyl]-2-oxo1-azetidinesulfonic acid; and
  3-[2-(2-amino-4-thiazolyl)-(Z)-2-(carboxymethoxyimino-acetamido)]-4-[(i-propoxycarbonyl)oxymethyl]-2-oxo-1-azetidinesulfonic acid.

6. A compound according to claim 5 wherein the absolute configuration with respect to carbon centers 3 and 4 is 3(S), 4(S).

7. A compound according to claim 6 selected from the group consisting of:
  (3S,4S)-3-[2-(2-amino-4-thiazolyl)-(Z)-2-carboxymethoxyiminoacetamido]-4-[(methoxycarbonyl)oxymethyl]-2-oxo-1-azetidinesulfonic acid and the potassium salt thereof;
  (3S,4S)-3-[1-(2-amino-4-thiazolyl)-(Z)-2-methoxyiminoacetamido]-4-[(methoxycarbonyl)oxymethyl]-2-oxo-1-azetidinesulfonic acid and the potassium salt thereof;
  (3S,4S)-3-[2-(2-amino-4-thiazolyl)-(Z)-2-[carboxymethoxyiminoacetamido]-4-[(aminoethoxycarbonyloxymethyl]-2-oxo-2-azetidinesulfonic acid; and
  (3S,4S)-3-[2-(2-amino-4-thiazolyl)-(Z)-2-[carboxymethoxyiminoacetamido]-4-[(carbamoyloxyethoxycarbonyl)oxomethyl]-2-oxo1-azetidinesulfonic acid.

8. A compound according to claim 1, 3-[D(-)-(α)-(4-ethyl-2,3-dioxo-1-piperizinocarbonylamino)-phenylacetamido]-4-[(methoxycarbonyl)oxymethyl]-2-oxo-1-azetidinesulfonic acid and the potassium salt thereof.

* * * * *